United States Patent [19]

Barr

[11] Patent Number: 5,811,313

[45] Date of Patent: Sep. 22, 1998

[54] IDENTIFICATION TEST FOR HIGHLY REFINED SESAME OIL

[75] Inventor: Mark Barr, Johnson City, Tenn.

[73] Assignee: King Pharmaceuticals, Inc., Bristol, Tenn.

[21] Appl. No.: 877,752

[22] Filed: Jun. 17, 1997

[51] Int. Cl.⁶ .............................. G01N 30/02; G01N 1/00; G01N 1/18
[52] U.S. Cl. ......................... 436/161; 436/174; 436/177; 436/178; 252/398; 424/439; 426/330; 426/330.6; 426/542; 426/545; 426/603; 426/605; 426/606; 426/607; 426/611; 426/615; 426/634; 549/386; 549/435; 549/464
[58] Field of Search ...................................... 549/386, 435, 549/464; 426/330, 330.6, 606, 542, 545, 667, 611, 601, 634, 629, 615, 603; 436/161, 177, 178, 174; 259/398; 424/439

[56] References Cited

U.S. PATENT DOCUMENTS 4,708,820  11/1987  Namiki et al. ............................ 252/398
5,180,588   1/1993  Shinmen et al. ........................ 424/439
5,209,826   5/1993  Ozaki et al. ............................... 203/38
5,211,953   5/1993  Shinmen et al. ........................ 424/439
5,336,496   8/1994  Akimoto et al. ..................... 424/195.1

Primary Examiner—Floyd D. Higel
Attorney, Agent, or Firm—Roberts & Brownell, LLC

[57] ABSTRACT

A method for confirming the presence of highly refined sesame oil in pharmaceuticals. By extracting, concentrating and detecting sesamin and epi-sesamin, through the method disclosed in the present invention, highly refined sesame oil can be identified. The disclosed method can be performed at room temperature and does not require over night extraction. In practice, the disclosed method entails extracting sesamin from a sample with an organic solvent, transferring and evaporating the solvent layer to dryness to form a residue. An alkyl halide is added to the residue to form a mixture. The mixture and an organic solvent are passed through a separating means, generating an eluent, the eluent is then evaporated to dryness to form a second residue. A 1:1 solution of an organic solvent and an alkyl halide is added to the second residue in a volume sufficient to form a concentrated extract. The concentrated extract is then analyzed with high performance liquid chromatography.

19 Claims, 9 Drawing Sheets

_5,811,313_

IDENTIFICATION TEST FOR HIGHLY REFINED SESAME OIL

FIELD OF THE INVENTION

This invention relates generally to a method of identifying the presence of Highly Refined sesame oil in pharmaceuticals. In particular, this invention relates to a method of extracting, concentrating and identifying sesamin in pharmaceuticals, wherein the method may be performed at room temperature.

BACKGROUND OF THE INVENTION

Sesame oil is a component of many pharmaceuticals currently on the market. FDA regulations require that these pharmaceuticals be tested to confirm the presence of sesame oil. The identification test generally used for the detection of sesame oil is the Baudouin test, which is based upon the appearance of a red color when a hydrogen chloride/sucrose mixture is shaken against sesame oil. The Villavecchia test is a modification of the Baudouin test, in that sucrose is replaced with furfural. A modified Villavecchia test is the AOAC official method 893.01 for sesame oil impurities in other oils.

The characteristic color reaction of the Baudouin and the Villavecchia test is due to the presence of sesamolin in the sesame oil. Sesamol is formed from sesamolin under certain processing conditions. Both sesamol and sesamolin are reported to posses antioxidative characteristics. The structure of sesamin is 2,6-(3,4-methylenedioxyphenyl)-cis-2,7-dioxabicyclo[3.3.0]octane and the structure of sesamolin is reported to be 2-(3,4-methylenedioxyphenoxy)-6(3,4-methylenedioxyphenyl)-cis-3,7-dioxabicyclo[3.3.0]octane, with the same tetrahydrofuran nucleus as in sesamin. The production of highly refined sesame oil includes that developed by Croda, Inc. using an improved means of refining sesame oil by passing it through a complex adsorption column of closely controlled activity. The product acquired through this process is known as Super Refined™ sesame oil. Hereinafter, sesame oils of especially high purity are broadly referred to as "highly refined sesame oil." It is desirable to use Highly refined sesame oil in pharmaceuticals due to the decreased level of impurities. Highly refined sesame oil passes all required monograph tests for sesame oil with the exception of the identification test. Highly refined sesame oil will not pass the Baudouin or Villavecchia identification tests due to the removal of sesamolin by the purification process.

The present invention provides an alternate identification test by high performance liquid chromatography ("HPLC") which positively identifies Highly refined sesame oil as sesame oil, and distinguishes it from other oils. This analytical method extracts the trace amounts of sesamin present in the highly refined sesame oil and concentrates it. The extract is then subjected to high performance liquid chromatography analysis. The identity of the highly refined sesame oil is confirmed by the presence of sesamin in the extract and by comparison of the chromatogram with a sesame oil identification standard.

SUMMARY OF THE INVENTION

It is therefore an object of the present invention to provide a method for positively identifying the presence of highly refined sesame oil in pharmaceuticals.

It is a further object of the present invention to provide a method for extracting and concentrating sesamin which is present in trace amounts in highly refined sesame oil.

It is a still further object of the present invention to provide a method for identifying the presence of highly refined sesame oil in pharmaceuticals which may be performed at room temperature.

It is a still further object of the present invention to provide a method for identifying the presence of highly refined sesame oil in pharmaceuticals where the extraction step of the method can be performed in less than an hour.

These and other objects of the present invention will become obvious to those skilled in the art upon review of the following disclosure.

DETAILED DESCRIPTION OF THE PREFERRED EMBODIMENT

To practice the present invention, it is first necessary to prepare a mobile phase to be used when performing high performance liquid chromatography analysis. To prepare a mobile phase, an organic solvent that is substantially immiscible with sesame oil, such as methanol, acetone, methyl ethyl ketone, diethyl ketone or ethanol is mixed with water. The combination is mixed thoroughly, filtered and degassed. In a preferred embodiment, one liter of mobile phase is prepared by thoroughly mixing 700 mL HPLC grade methanol and 300 mL HPLC grade water. The resulting mixture is then filtered and degassed through means known to those skilled in the art, such as filtering the solution through a 0.45 µm nylon membrane filter and degassing by a means such as sonication, vacuum or sparging with helium gas.

Figure 1:
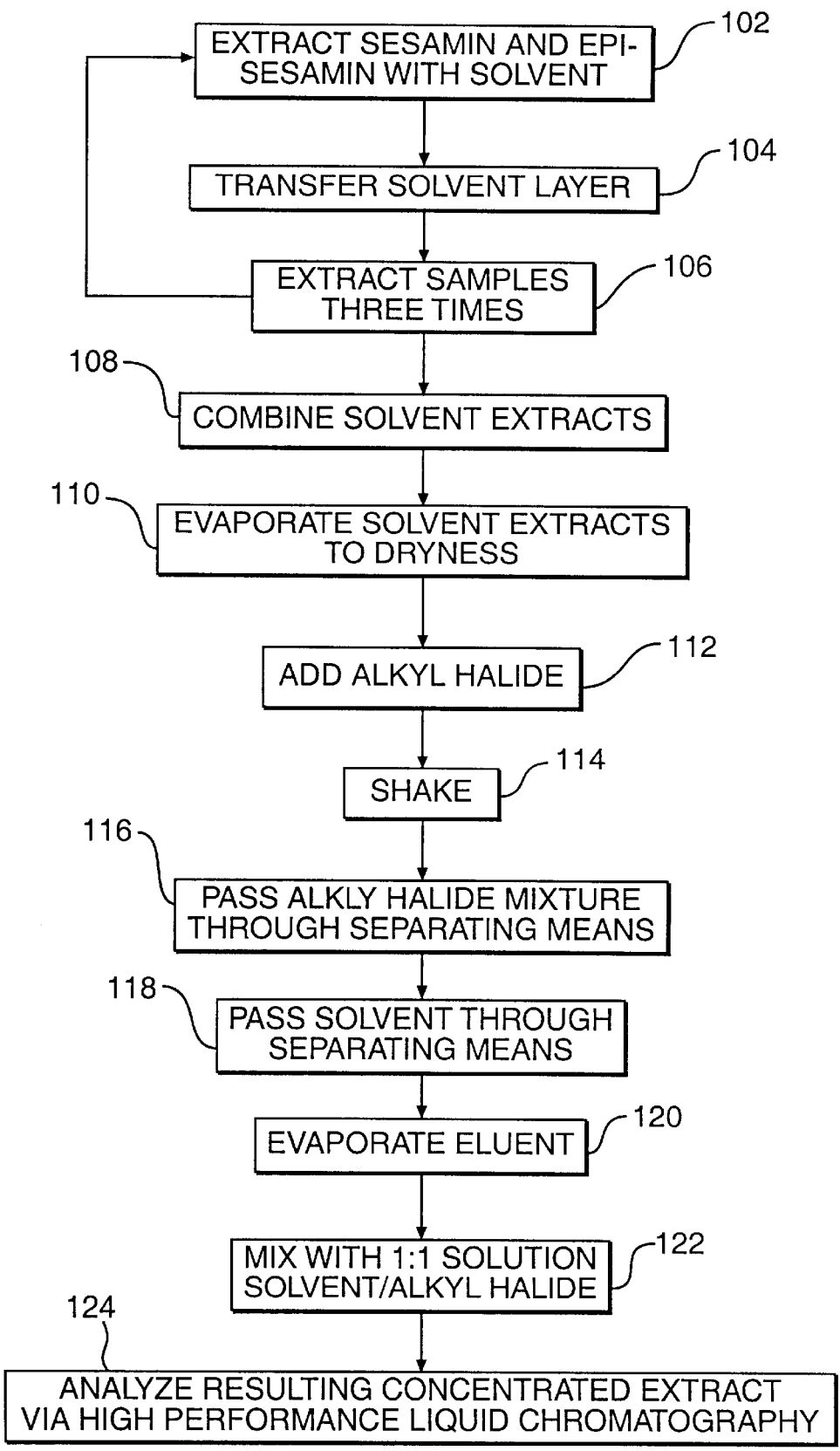
FIG. 1 is a flow chart depicting the method of the present invention.
Figure 2:
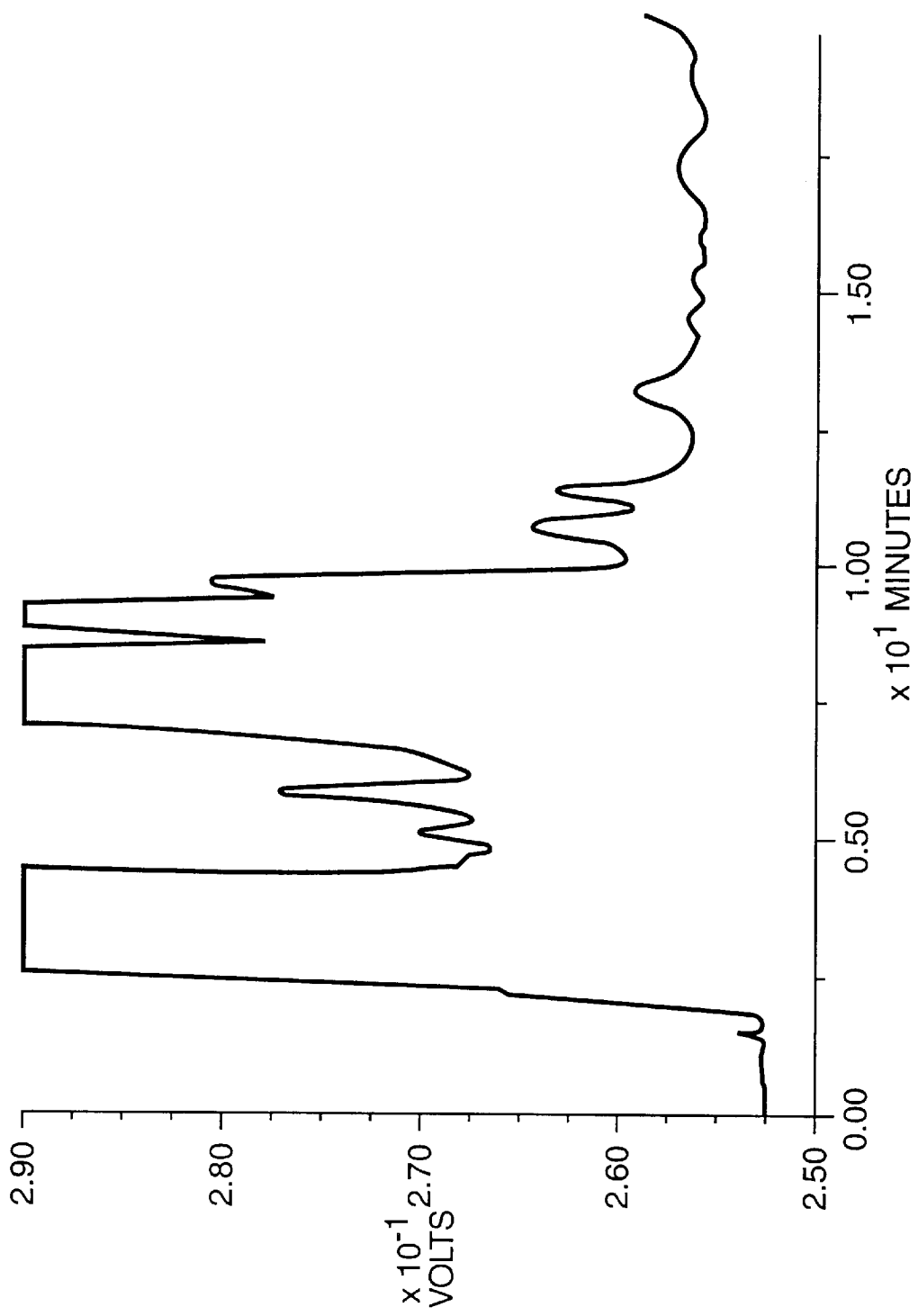
FIG. 2 shows the identification test results for tung oil.
Figure 3:
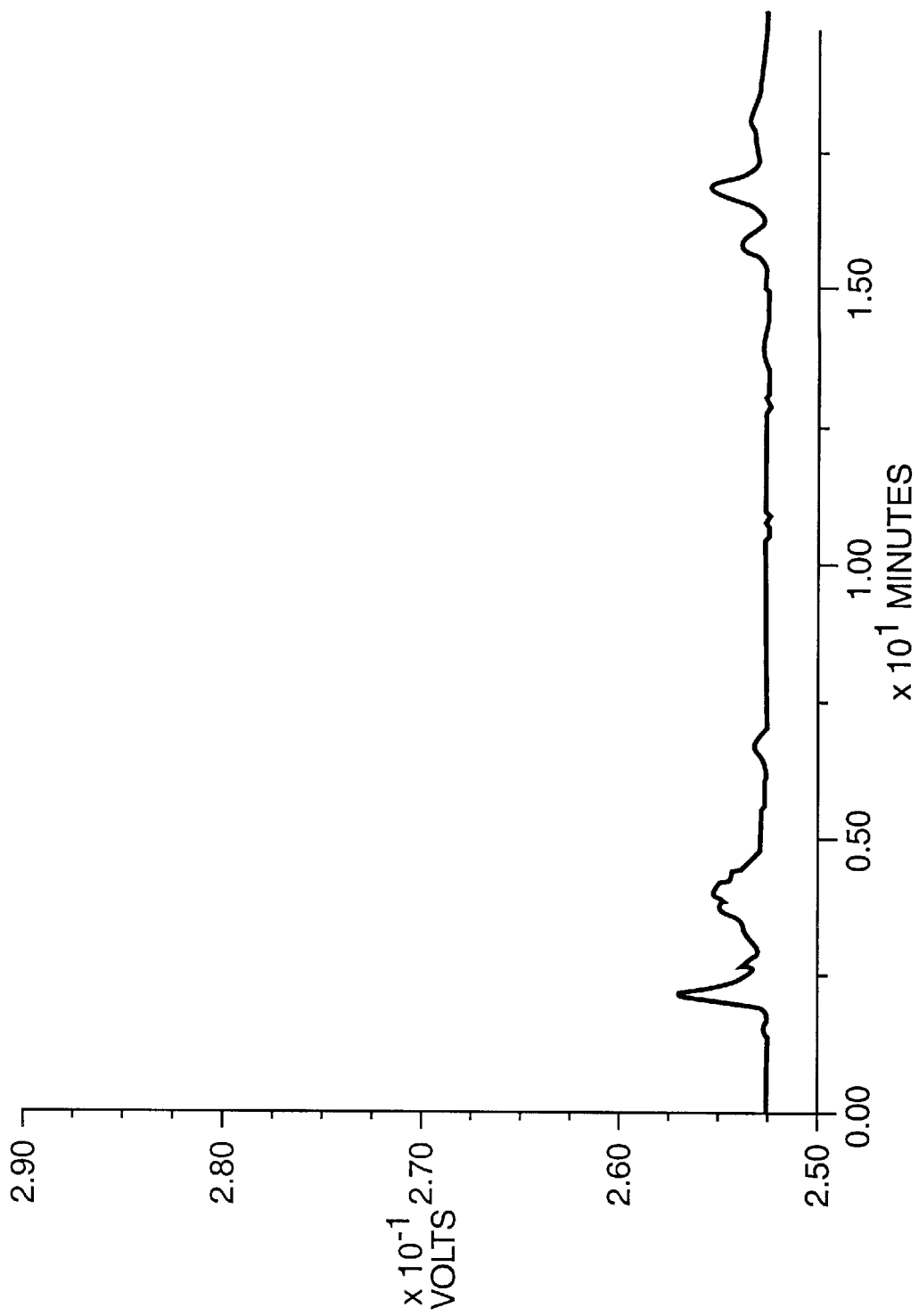
FIG. 3 shows the identification test results for cottonseed oil.
Figure 4:
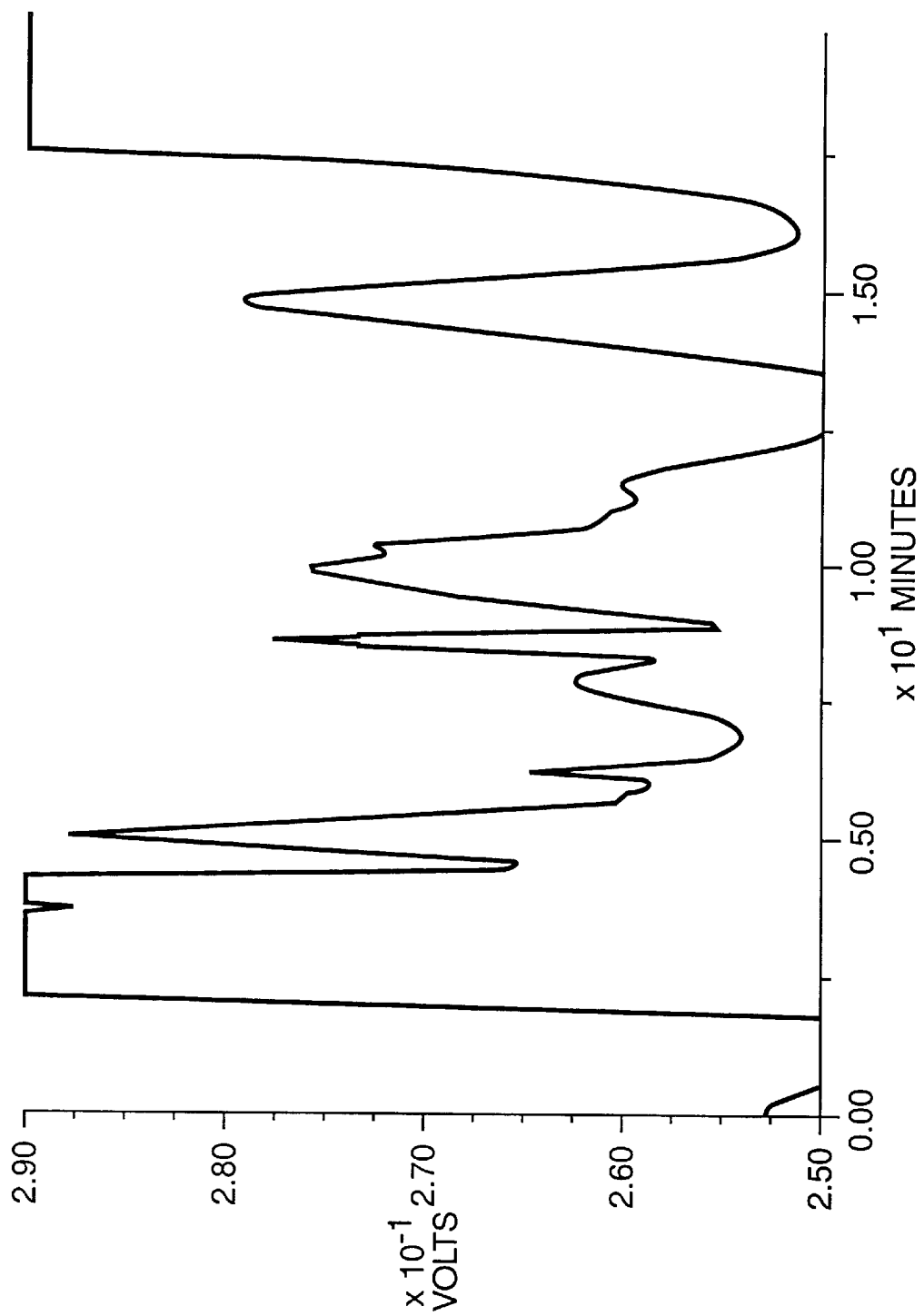
FIG. 4 shows the identification test results for linseed oil.
Figure 5:
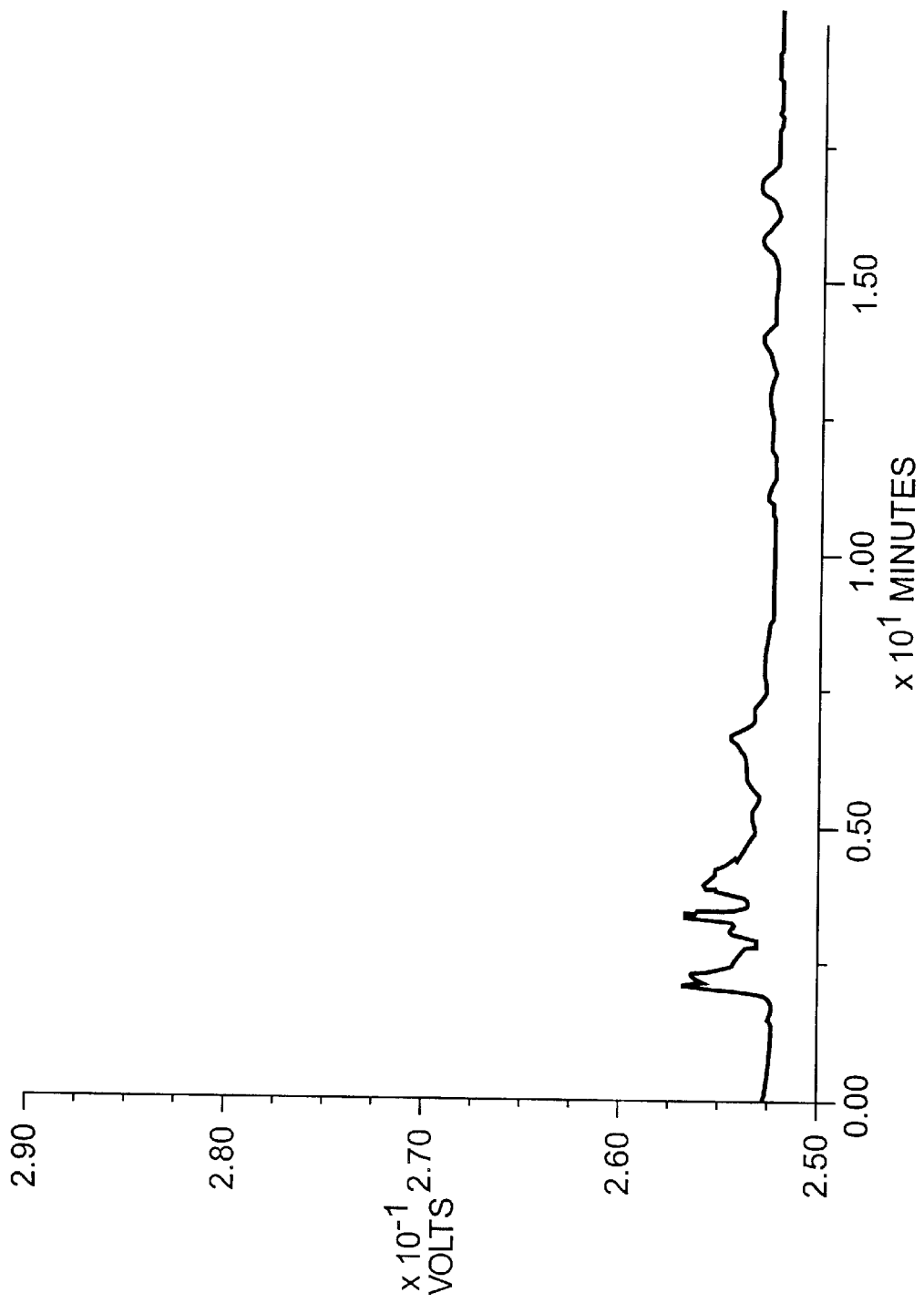
FIG. 5 shows the identification test results for soybean oil.
Figure 6:
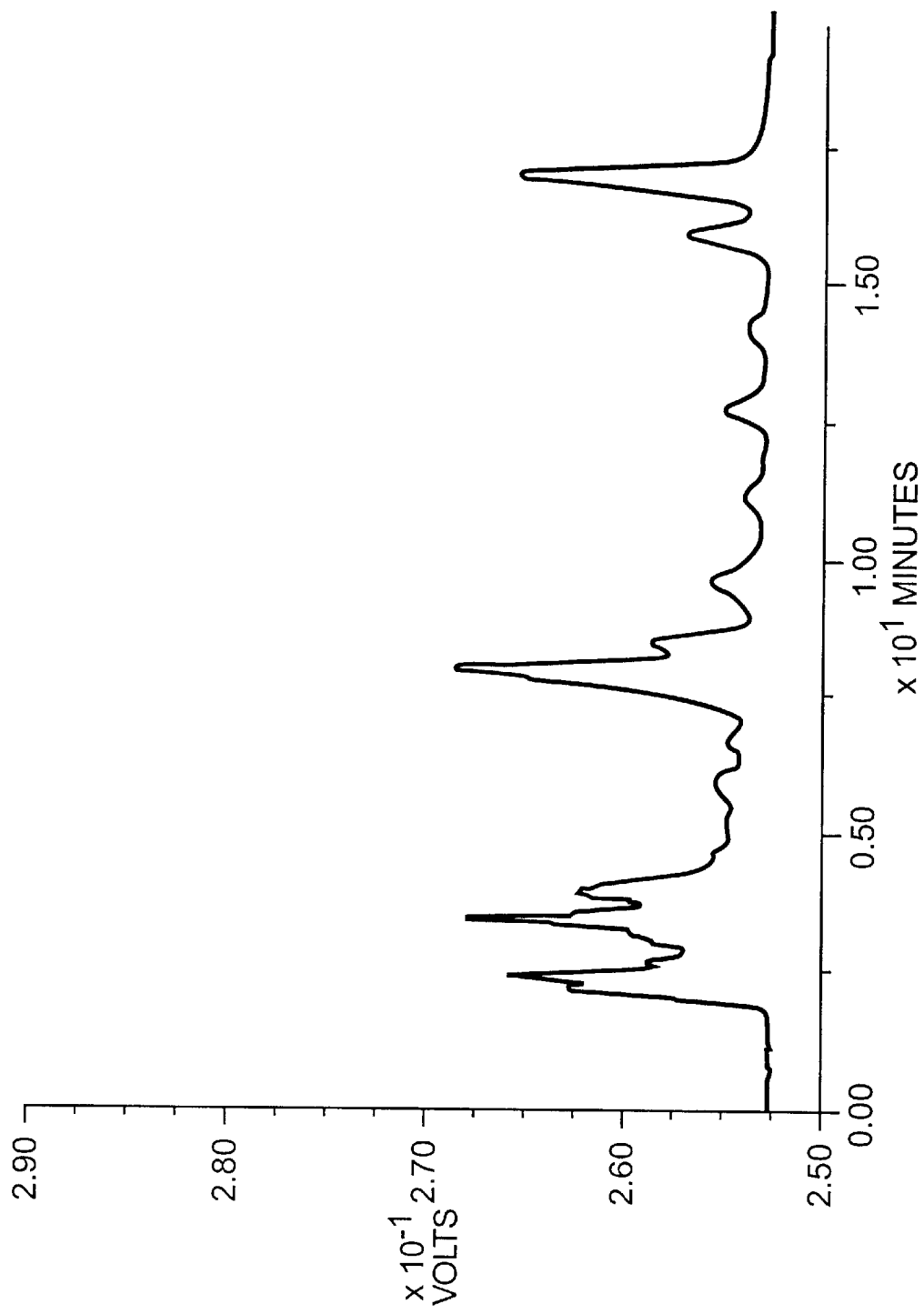
FIG. 6 shows the identification test results for olive oil.
Figure 7:
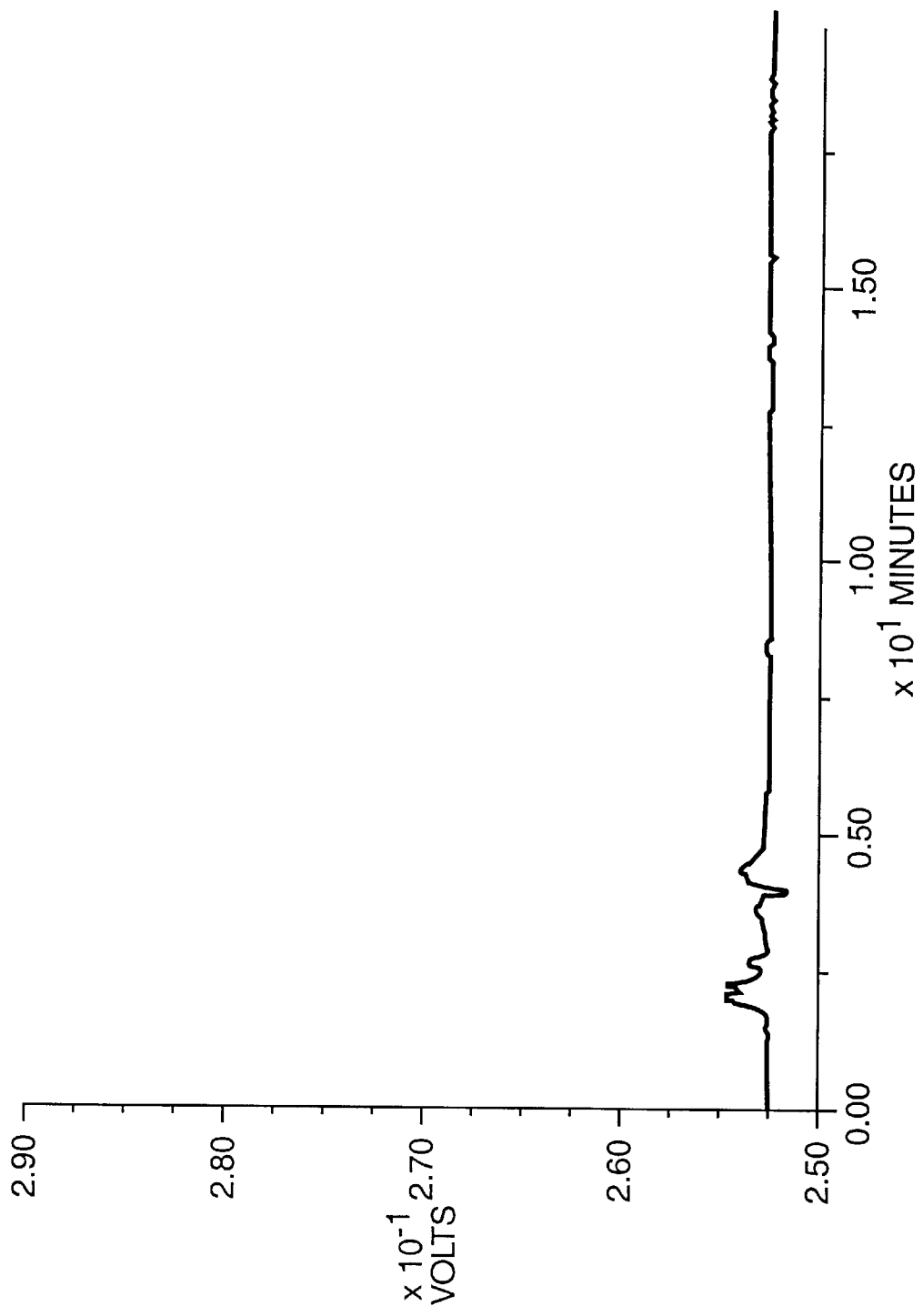
FIG. 7 shows the identification test results for mineral oil.
Figure 8:
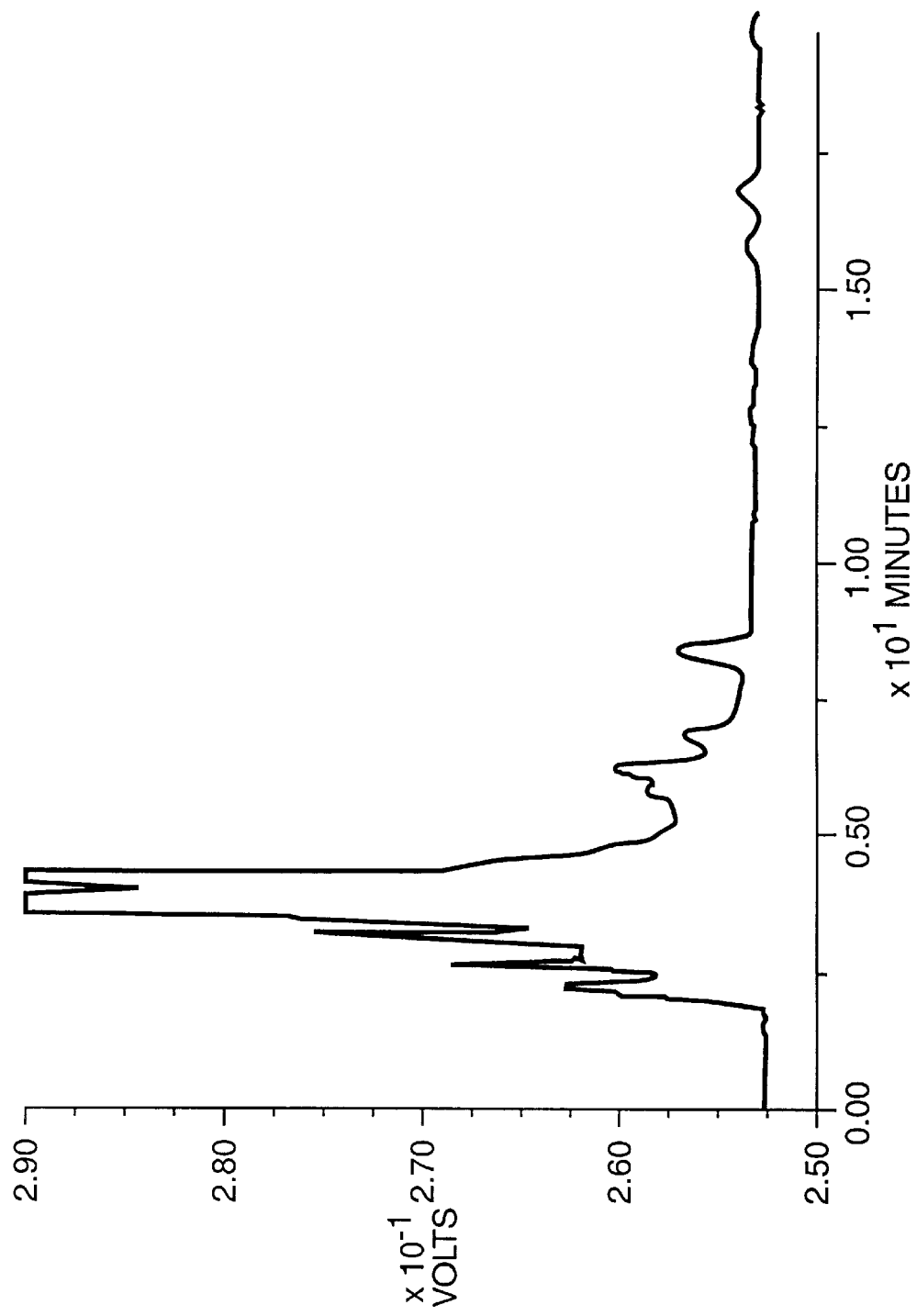
FIG. 8 shows the identification test results for safflower oil.

It is then necessary to prepare the standard(s) and sample (s). Referring to FIG. 1, highly refined sesame oil and sesame oil standard are transferred into separate disposable centrifuge tubes. In a preferred embodiment, approximately 10 mL of highly refined sesame oil is transferred using a 10-ml disposable syringe, and 1 mL of sesame oil standard (Sigma or equivalent) is transferred using a 1 mL disposable syringe.

The sesamin and epi-sesamin are extracted 102 from the samples by adding an organic solvent that is substantially immiscible with sesame oil. In a preferred embodiment, sesamin and epi-sesamin are extracted by adding 3 mL methanol to each tube. The solution is shaken vigorously for approximately 30 to 60 seconds, and centrifuged for approximately ten minutes. After centrifuging, the solvent layer is transferred 104 by transferring the top organic solvent layer of each tube to separate screw-capped test tubes. The samples are reextracted two more times 106, with each extraction process an organic solvent is added and the resulting solution is shaken vigorously and centrifuged. In a preferred embodiment, 3 mL of methanol is used for each extraction. The solvent extracts are combined 108 and evaporated to dryness 110 by an evaporating means. Varying evaporating means are well known by those skilled in the art and include a steam bath under a stream of nitrogen, as well as other means that allow for evaporation of the solvent. An alkyl halide such as methylene chloride is then added to each test tube 112. The tubes are capped and shaken 114 vigorously for approximately 30 to 60 seconds. In a preferred embodiment, five mL of methylene chloride is used.

Using a 5-mL disposable syringe, 5 mL of the alkyl halide mixture is then passed through separating means 116 in order to prepare the cartridges for extraction. Separating means are well known to those skilled in the art and can include solid phase extraction. In a preferred embodiment the separating means comprises two Waters Sep-Pak® silica cartridges. One Sep-Pak is used for the sample, the other for the standard.

Using a 5-mL disposable syringe equipped with needle, the entire contents of the tube are withdrawn. The contents of the syringe are passed through the Sep-Pak exerting sufficient pressure to collect the eluent dropwise into another test tube. This eluent is discarded. 5 mL of solvent is passed through the separating means 118 using a 5-mL disposable syringe. Sufficient pressure to exerted to allow the eluent to collect dropwise into another test tube. The eluent 120 is evaporated to dryness by an evaporating means, such as a steam bath under a stream of nitrogen.

1 mL of a 1:1 methanol/methylene chloride mixture is next added to the test tube containing the highly refined sesame oil extract 122. The solution is shaken vigorously to mix. The solution is then analyzed through high performance liquid chromatrography 124.

5 mL of the methanol/methylene chloride mixture is then added to the test tube containing the sesame oil standard extract. The resulting solution is then shaken vigorously to mix. One mL of this mixture is pippetted to another test tube. 14 mL of the methanol/ methylene chloride mixture is then added. The resulting solution is then shaken vigorously to mix. Once the solution is mixed it is analyzed through high performance liquid chromatography.

Instrumentation required for high performance liquid chromatography is readily available and understood by those skilled in the art. In a preferred embodiment the following parameters are used:

Column: Resolve $C_{18}$, 3.9 mm x 300 mm, $5\mu$

Wavelength: 290 nm

Flow Rate: 0.8 mL/Minute

Injection Volume: $20\mu L$

Approximate Run Time: 25 Minutes

Attenuation: Attenuate to Suitable Peak Size It is understood however, that the chromatographic technique of HPLC is well known to those skilled in the art, and that any or all of the above parameters may be altered.

When using the aforementioned parameters, the sample meets the identification requirements if the tallest peak in the chromatogram of the sample elutes at approximately 10 to 15 minutes and the retention time of this peak and the adjacent peak downfield are similar to the retention times of these same peaks in the standard chromatogram. The peak at 10 to 15 minutes and its adjacent downfield neighbor are sesamin and epi-sesamin.

Example 1, Specificity

Specificity tests were performed by analyzing various oils obtained from Sigma or Aldrich Chemical Company to determine whether these oils could be mistakenly identified as highly refined sesame oil using the disclosed identification test. The oils used for specificity testing included tung, cottonseed, linseed, soybean, olive, mineral and safflower oil. The highly refined sesame oil was the only oil tested that would pass the disclosed identification method.

Referring to FIGS. 2, 3, 4, 5, 6, 7, and 8, the identification test results of tung, cottonseed, linseed, soybean, olive, mineral and safflower oil, respectively, are shown.

Figure 9:
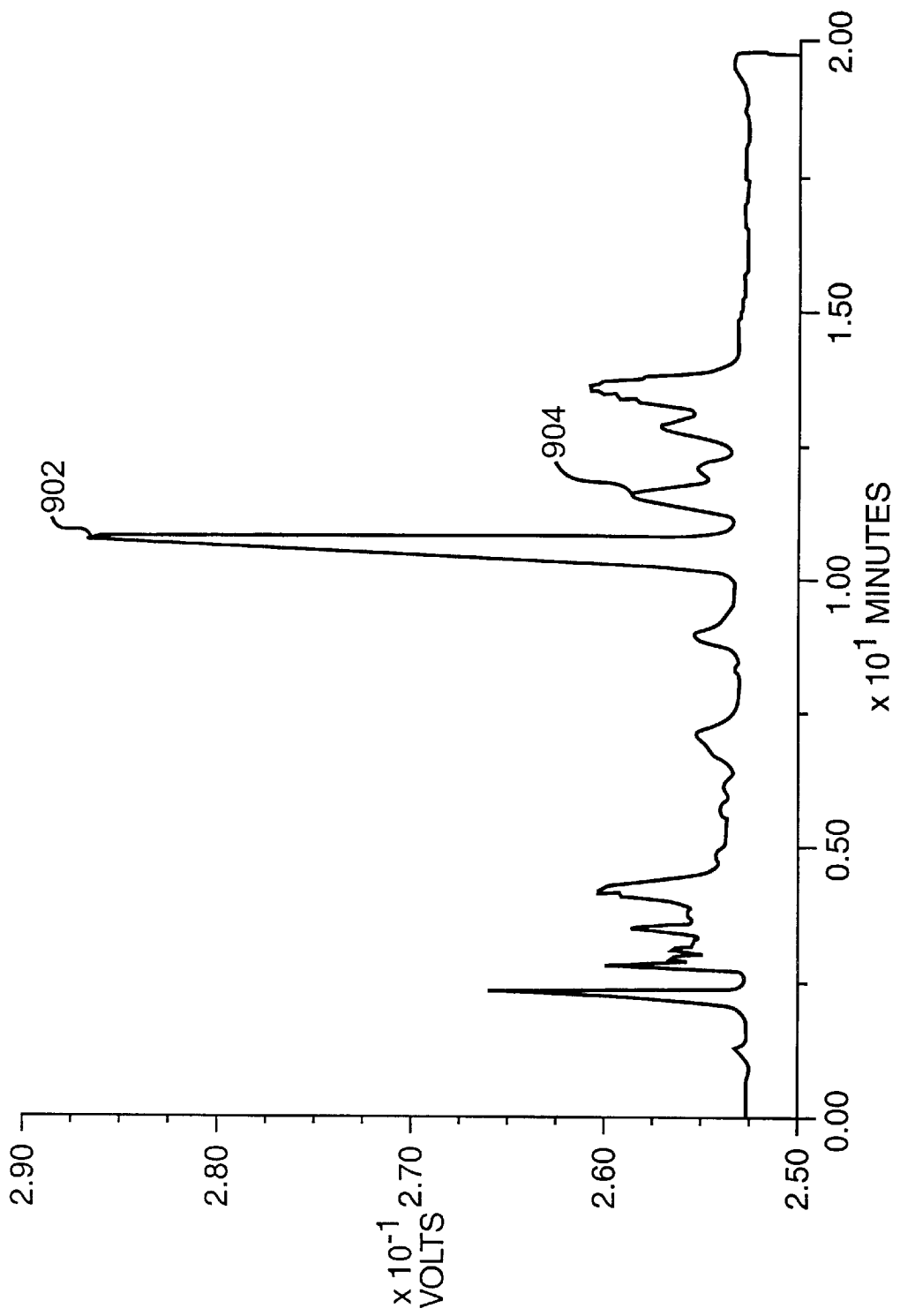
FIG. 9 shows the identification test results for highly refined sesame oil.

Referring to FIG. 9 the identification test results of highly refined sesame oil, including the sesamin peak 902 at approximately ten minutes and the epi-sesamin peak 904 at approximately eleven minutes are shown.

Example 2, Method Precision

Method precision tests were performed by preparing six replicate samples for the same sesame oil. Each sample was taken through the entire procedure and chromatographed. The chromatograms obtained from these six separate samples were quite similar. The results of the two peaks of interest are shown below:

TABLE 1

Method Precision Results for Sesamin and Epi-sesamin

| AVERAGE PEAK AREA | | AVERAGE RETENTION TIME (Minutes) | |
|---|---|---|---|
| sesamin | epi-sesamin | sesamin | epi-sesamin |
| 1576908 | 230545 | 14.64 | 16.48 |
| 1581303 | 232289 | 14.71 | 16.56 |
| 1541247 | 224342 | 14.76 | 16.63 |
| 1559363 | 228304 | 14.76 | 16.62 |
| 15530815 | 224036 | 14.78 | 16.66 |
| 1571475 | 230790 | 14.78 | 16.66 |
| RSD: 1.3% | 1.5% | 0.4% | 0.4% |

Although the method of the present invention has been described in detail for purpose of illustration, it is understood that such detail is solely for that purpose, and variations can be made therein by those skilled in the art without departing from the scope of the invention. The method of the present invention is defined by the following claims.

What is claimed is:

1. A method of detecting the presence of highly refined sesame oil, comprising:

extracting sesamin from a sample with a first organic solvent, wherein, the first organic solvent is at least one selected from the group consisting of methanol. acetone, methyl ethyl ketone, diethyl ketone or ethanol, to create a solvent layer and a waste layer;

transferring the solvent layer;

evaporating the solvent layer to dryness to form a first residue;

adding an alkyl halide to the first residue to form a mixture;

passing the resultant mixture through a separating means;

passing a second organic solvent, wherein the second organic solvent is at least one selected from the group consisting of methanol, acetone, methyl ethyl ketone, diethyl ketone or ethanol, through the separating means to generate an eluent;

evaporating the eluent to dryness to form a second residue;

adding a 1:1 solution comprising a third organic solvent, wherein the third organic solvent is at least one selected from the group consisting of methanol, acetone, methyl ethyl ketone, diethyl ketone or ethanol and an alkyl halide to the second residue in a volume sufficient to form a concentrated extract; and analyzing the concentrated extract with high performance liquid chromatography.

2. The method of detecting the presence of highly refined sesame oil as claimed in claim 1, wherein the first organic solvent, the second organic solvent and the third organic solvent are substantially immiscible with sesame oil.

3. The method of detecting the presence of highly refined sesame oil as claimed in claim 1, wherein extracting sesamin from a sample further comprises:

adding a fourth organic solvent to the sample, wherein the fourth organic solvent is at least one selected from the group consisting of methanol, acetone, methyl ethyl ketone, diethyl ketone or ethanol:

shaking the sample; and centrifuging the sample.

4. The method of detecting the presence of highly refined sesame oil as claimed in claim 3, wherein the sample is shaken for about 30 to 60 seconds.

5. The method of detecting the presence of highly refined sesame oil as claimed in claim 3, wherein the sample is centrifuged for about ten minutes.

6. The method of detecting the presence of highly refined sesame oil as claimed in claim 1, wherein the means for evaporating the solvent layer to dryness is a steam bath under a stream of nitrogen.

7. The method of detecting the presence of highly refined sesame oil as claimed in claim 1, wherein the separating means is a silica cartridge.

8. The method of detecting the presence of highly refined sesame oil as claimed in claim 1, wherein the alkyl halide is methylene chloride.

9. The method of detecting the presence of highly refined sesame oil as claimed in claim 1, wherein analyzing the concentrated extract with high performance liquid chromatography further comprises:

injecting the concentrated extract into a column having a mobile phase; and detecting the elution of sesamin and epi-sesamin with a detector.

10. The method of detecting the presence of highly refined sesame oil as claimed in claim 9, wherein the column is a Resolve $C_{18}$ 3.9 mm x 300 mm, $5\mu$.

11. The method of detecting the presence of highly refined sesame oil as claimed in claim 9, wherein preparation of the mobile phase comprises:

adding a fifth organic solvent, wherein the fifth organic solvent is at least one selected from the group consisting of methanol, acetone, methyl ethyl ketone, diethyl ketone or ethanol to water to form a solution;

mixing the solution;

filtering the solution; and degassing the solution.

12. The method of detecting the presence of highly refined sesame oil as claimed in claim 9, wherein the mobile phase has a flow rate of about 0.8 milliliter per minute.

13. The method of detecting the presence of highly refined sesame oil as claimed in claim 9, wherein the detector is a spectrophotometer measuring absorbency at a wavelength of about 290 nanometers.

14. The method of detecting the presence of highly refined sesame oil as claimed in claim 10, wherein injecting the concentrated extract into the column having the mobile phase comprises injecting about 20 $\mu$l of the concentrated extract into the column.

15. The method of detecting the presence of highly refined sesame oil as claimed in claim 1, comprising:

repeating the extracting and transferring steps a plurality of times; and combining the solvent layers generated from the extracting and transferring steps.

16. The method of detecting the presence of highly refined sesame oil as claimed in claim 11, wherein filtering the solution comprises: passing the solution through a 0.45 $\mu$m nylon membrane.

17. The method of detecting the presence of highly refined sesame oil as claimed in claim 11, wherein degassing the solution comprises: sparging the solution with helium gas.

18. The method of detecting the presence of highly refined sesame oil as claimed in claim 1, wherein the method is performed at room temperature.

19. The method of detecting the presence of highly refined sesame oil as claimed in claim 1, wherein extracting the sesamin takes less than one hour.

* * * * *